US00PP34144P2

(12) United States Plant Patent
Wood

(10) Patent No.: US PP34,144 P2
(45) Date of Patent: Apr. 19, 2022

(54) ***RHAPHIOLEPIS* PLANT NAMED 'SMNRICS'**

(50) Latin Name: *Rhaphiolepis indica*
Varietal Denomination: SMNRICS

(71) Applicant: Spring Meadow Nursery, Inc., Grand Haven, MI (US)

(72) Inventor: Timothy D Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/483,155

(22) Filed: Sep. 23, 2021

(51) Int. Cl.
*A01H 5/02* (2018.01)
*A01H 6/74* (2018.01)

(52) U.S. Cl.
USPC ..... Plt./254
CPC ..... *A01H 6/74* (2018.05)

(58) Field of Classification Search
USPC ..... Plt./254
CPC ..... A01H 6/74; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Rhaphiolepis* plant named 'SMNRICS' is disclosed, characterized by abundant, bright pink flowers, and glossy, dark green leaves. Plants have a compact, ground-hugging growth habit. The new variety is a *Rhaphiolepis*, typically produced as an ornamental plant.

2 Drawing Sheets

Latin name of the genus and species: *Rhaphiolepis indica*.
Variety denomination: 'SMNRICS'.

BACKGROUND OF THE INVENTION

The new *Rhaphiolepis* cultivar is a product of a planned breeding program conducted by the inventor. The objective of the breeding program was to produce new *Rhaphiolepis* cultivars with increased flower number, and compact, spreading habits. The open-pollination resulting in this new variety was made in 2010, at a commercial nursery in Grand Haven, Mich.

The parents cannot be identified as this new selection resulted from an open pollination in which seed was bulk collected. The new cultivar was found and selected by the inventor in 2015 at the same nursery in Grand Haven, Mich.

Asexual reproduction of the new cultivar 'SMNRICS' was first performed in 2015 in Grand Haven, Mich., by softwood cuttings. Subsequent propagation has shown that the unique features of this cultivar are stable and reproduced true to type in successive generations.

SUMMARY OF THE INVENTION

The cultivar 'SMNRICS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNRICS'. These characteristics in combination distinguish 'SMNRICS' as a new and distinct *Rhaphiolepis* cultivar:

1. Compact growth.
2. Dense branching.
3. Somewhat spreading, ground-hugging habit.
4. Glossy, dark green leaves.
5. Reblooming.

PARENT COMPARISONS

Parental comparisons are unavailable, as both parents are unidentified.

COMMERCIAL COMPARISONS

Plants of 'SMNRICS' are similar in some horticultural characteristics to the variety *Rhaphiolepis* 'Eleanor Tabor', unpatented. The new variety, however, differs in the following:

1. The new variety has a slightly spreading habit, while this comparator has a less spreading and more upright habit.
2. The new variety has an abundance of pink flowers, while this comparator produces less flowers.
3. Flowers of the new variety are a darker pink than flowers of this comparator.

BRIEF DESCRIPTION OF THE PHOTOGRAPHS

'SMNRICS' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

DETAILED BOTANICAL DESCRIPTION

Figure 1:
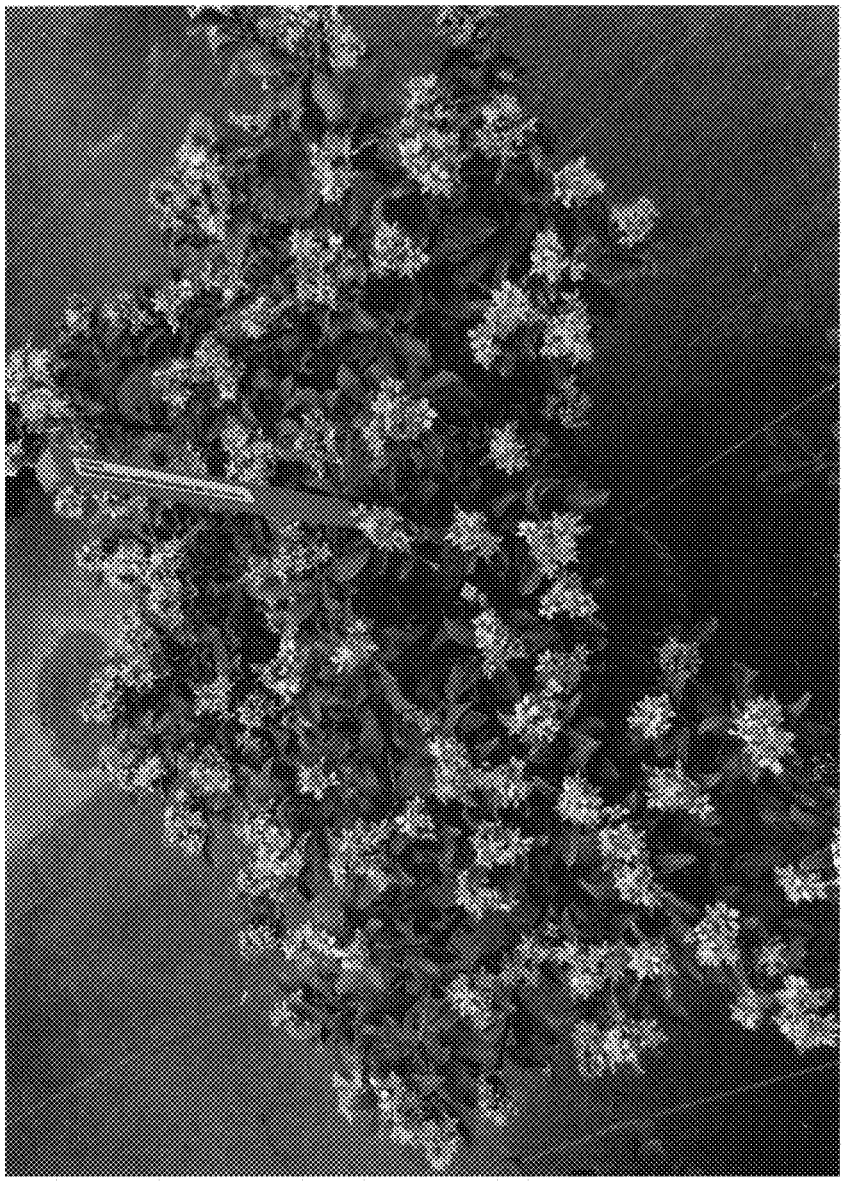
FIG. 1 shows a container grown flowering plant of 'SMNRICS' grown outdoors in Grand Haven, Mich. at about 2 years of age.
Figure 2:
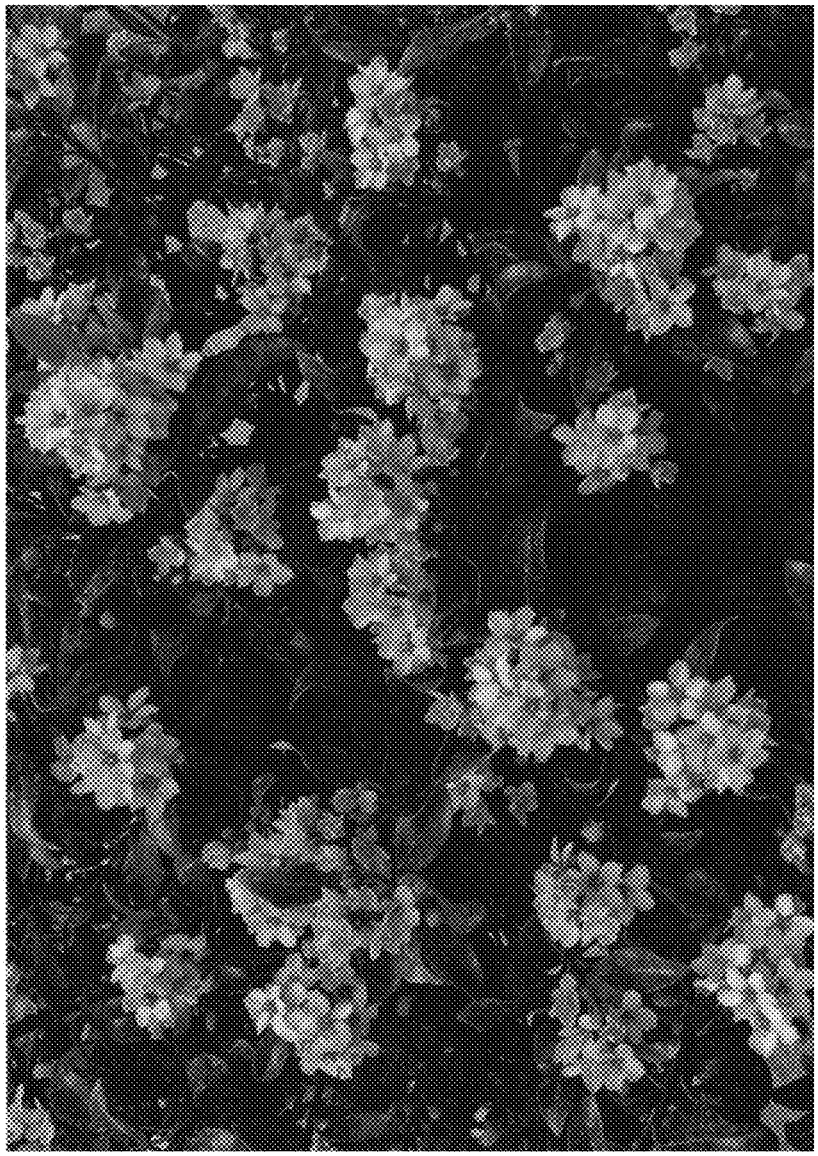
FIG. 2 shows the mature inflorescences of a container-grown plant of 'SMNRICS', grown in Grand Haven, Mich.

In the following description, color references are made to The Royal Horticultural Society Colour Chart 2015, except where general terms of ordinary dictionary significance are used. The following observations and measurements describe a 'SMNRICS' plant. This plant was grown in a poly-greenhouse in a 3 gallon container, in Grand Haven, Mich. The plant described is approximately 1-2 years old. Temperatures ranged from 5-10° C. at night and 18° C. to 27° C. during the day. No artificial light, photoperiodic treatments were given to the plants. Measurements and numerical values represent averages of typical plant types. Botanical classification: *Rhaphiolepis indica* 'SMNRICS'.

PROPAGATION

Time to initiate roots: 4 to 6 weeks.
Time to produce a rooted plant: 2 to 3 months during the Summer.
Root description: Fibrous, moderately free-branching, moderately dense, medium thickness. Brown in color, not effectively measured with a color chart.

PLANT

Plant type: Perennial shrub.
Age of plant described: Approximately 1 to 2 years old.
Plant shape: Upright, compact.
Growth habit: Upwards, slightly outwards.
Height: 25 cm.
Plant spread: 25 to 30 cm.
Growth rate: Good.
Plant vigor: Fairly vigorous.
Branching characteristics: Free basal branching, no pinching required.
Length of lateral branches: 10 to 15 cm.
Diameter of lateral branches: 3 to 5 mm.
Quantity of lateral branches: 15.
Internode length: 1 to 2 cm.
Stem:
- *Appearance/shape.*—Round.
- *Aspect.*—20 to 45°.
- *Strength.*—Strong.
- *Color.*—New Growth: RHS Yellow-Green 144B with some Greyed-Orange 176D. Old Growth: RHS Greyed-Green 197C, with 197B streaks.
- *Pubescence.*—Some, on new growth only.

FOLIAGE

Leaf:
- *Arrangement.*—Sub-opposite and alternate; single.
- *Quantity.*—10.
- *Average length.*—4 cm.
- *Average width.*—2 cm.
- *Pubescence.*—Only on new leaves, both sides.
- *Shape.*—Oblong to elliptic.
- *Apex.*—Obtuse to slightly acute.
- *Base.*—Attenuate.
- *Margin.*—Entire.
- *Texture.*—Leathery with venation, both sides.
- *Color.*—Young, Upper side: RHS Brown 200D, with Greyed-Orange 175B tinge near margins, and Grey-Brown 199C pubescence. Young, Under side: RHS Brown 200D, with Greyed-Orange 175B tinge near margins, and Grey-Brown 199C pubescence. Mature, Upper side: RHS Yellow-Green 147A. Mature, Under side: RHS Yellow-Green 146D.
- *Venation.*—Type: Pinnate. Color, Upper side: RHS Yellow-Green 146C. Color, Under side: RHS Yellow-Green 146C.

Petiole:
- *Length.*—1 cm.
- *Diameter.*—2 mm.
- *Color.*—Upper Surface: RHS Yellow-Green 146C. Lower Surface: RHS Yellow-Green 146C.
- *Texture.*—Smooth and slightly leathery, both surfaces.

FLOWER

Natural flowering season: Spring.
Flower:
- *Arrangement.*—Single flowers in groups of panicles.
- *Form.*—Star-shaped.
- *Inflorescence type.*—Panicles.
- *Inflorescence height.*—5 cm.
- *Inflorescence width.*—5 cm.
- *Flowers per inflorescence.*—15 to 20.
- *Flowers per lateral stem.*—15 to 20.
- *Flowers and buds per plant.*—About 200.
- *Persistent or self-cleaning.*—Self-cleaning.
- *Fragrance.*—Very light, sweet.
- *Aspect.*—Upward and slightly outward.
- *Diameter.*—2 cm.
- *Length.*—2 cm.
- *Depth.*—5 mm.

Bud:
- *Buds per lateral stem.*—15 to 20.
- *Shape.*—Egg-shaped.
- *Length.*—5 mm.
- *Diameter.*—2 mm.
- *Color.*—RHS Red-Purple 73B.

Petals:
- *Quantity.*—5.
- *Appearance.*—Soft, delicate.
- *Arrangement.*—Whorl.
- *Length.*—11 mm.
- *Width.*—4 mm.
- *Shape.*—Spatulate/ovate.
- *Apex.*—Acute.
- *Base.*—Truncate.
- *Margin.*—Entire.
- *Texture.*—Soft, smooth on both sides.
- *Color.*—When Opening, Upper Surface: RHS Red-Purple 73B and 73D. When Opening, Lower Surface: RHS Red-Purple 73B and 73D. Fully Opened, Upper Surface: RHS Red-Purple 73B and 73D. Fully Opened, Lower Surface: RHS Red-Purple 73B and 73D.

Petaloids: None.
Sepals:
- *Appearance.*—Whorl, recurve down.
- *Arrangement.*—Whorl.
- *Quantity.*—5.
- *Length.*—5 mm.
- *Width.*—2 mm.
- *Shape.*—Narrowly triangular.
- *Margin.*—Entire.
- *Apex.*—Acute.
- *Base.*—Truncate.

*Color*.—Mature, Upper Side: RHS Yellow-Green N144C, with Greyed-Red 179A. Mature, Under Side: RHS Yellow-Green N144C, with Greyed-Red 179A.

*Texture*.—Smooth, both surfaces.

Calyx:

*Shape*.—Cup-like.

*Length*.—4 mm.

*Width*.—5 mm.

Peduncles:

*Length*.—2 cm.

*Diameter*.—2 mm.

*Angle*.—Around 45°.

*Strength*.—Good.

*Texture*.—Smooth, some pubescence.

*Color*.—RHS Yellow-Green 144A.

Pedicels:

*Length*.—5 mm.

*Diameter*.—1 mm.

*Angle*.—Around 45°.

*Strength*.—Flexible.

*Texture*.—Pubescent.

*Color*.—RHS Yellow-Green 144A.

REPRODUCTIVE ORGANS

Stamens:

*Number*.—10 to 15.

*Filament length*.—4 mm.

*Filament color*.—RHS White 155B.

Anthers:

*Shape*.—Flat.

*Length*.—1 mm.

*Color*.—RHS Yellow 4B.

*Pollen color*.—RHS Yellow 4B.

*Pollen amount*.—Moderate.

Pistil:

*Number*.—2.

*Length*.—7 mm.

*Style*.—Length: 7.9 mm. Color: RHS White 155B.

*Stigma*.—Shape: Round, very small. Color: RHS White 155B.

OTHER CHARACTERISTICS

Seeds: Not observed.

Fruit:

*Length*.—1 cm.

*Diameter*.—1 cm.

*Color*.—Before Ripe: Mix of RHS Yellow-Green 144B and Greyed-Red 187B. Ripe: RHS Violet N92A.

Texture: Smooth.

Disease/pest resistance: No resistance nor susceptibility to normal diseases and pests of *Rhaphiolepis* have been observed.

Temperature tolerance: Typically USDA Zones 8 to 10.

What is claimed is:

1. A new and distinct cultivar of *Rhaphiolepis* plant named 'SMNRICS' as herein illustrated and described.

* * * * *